United States Patent [19]

Suzuki et al.

[11] Patent Number: 4,664,773
[45] Date of Patent: May 12, 1987

[54] AIR-TO-FUEL RATIO SENSOR FOR AN AUTOMOBILE

[75] Inventors: Seiko Suzuki, Hitachiohta; Takao Sasayama, Hitachi; Masayuki Miki, Katsuta, all of Japan

[73] Assignee: Hitachi, Ltd., Tokyo, Japan

[21] Appl. No.: 826,667

[22] Filed: Feb. 6, 1986

[30] Foreign Application Priority Data

Feb. 6, 1985 [JP] Japan .................................. 60-19882

[51] Int. Cl.⁴ ............................................. G01N 27/58
[52] U.S. Cl. ..................................... 204/406; 204/425
[58] Field of Search ........................... 204/406, 425, 15

[56] References Cited

U.S. PATENT DOCUMENTS

| | | | |
|---|---|---|---|
| 4,272,329 | 6/1981 | Hetrick et al. | 204/1 T |
| 4,272,330 | 6/1981 | Hetrick | 204/1 T |
| 4,272,331 | 6/1981 | Hetrick | 204/1 T |
| 4,396,466 | 8/1983 | Hetrick et al. | 204/1 T |
| 4,440,621 | 4/1984 | Kitahara et al. | 204/406 |
| 4,578,171 | 3/1986 | Yamada et al. | 204/406 |
| 4,578,172 | 3/1986 | Yamada et al. | 204/412 |
| 4,586,476 | 5/1986 | Asayama et al. | 123/440 |
| 4,591,421 | 5/1986 | Yamada et al. | 204/406 |
| 4,594,139 | 6/1986 | Asayama et al. | 204/410 |

Primary Examiner—G. L. Kaplan
Attorney, Agent, or Firm—Antonelli, Terry & Wands

[57] ABSTRACT

An A/F sensor for an automobile comprises means for providing an electrical potential higher than ground on the sensing electrode such that the sensor is able to detect air-fuel ratios over the entire spectrum of such ratios from lean through rich.

13 Claims, 16 Drawing Figures $\lambda < 1$

ATMOSPHERE      EXHAUST GAS $\lambda = 1$

ATMOSPHERE      EXHAUST GAS $\lambda > 1$

ATMOSPHERE      EXHAUST GAS

AIR-TO-FUEL RATIO SENSOR FOR AN AUTOMOBILE

FIELD OF THE INVENTION

The present invention relates to a sensor for an A/F control apparatus of an internal combustion engine and, more particularly an A/F sensor for an automobile which facilitates detecting A/F in three conditions, a rich region, theoretical A/F and a lean region, in a wide range.

BACKGROUND OF THE INVENTION

It is desirable that an internal combustion engine be operated in a rich region in which an excess air rate $\lambda$ is $\lambda<1$, at $\lambda=1$ (a theoretical A/F) and in a lean region in which $\lambda<1$ corresponding to the conditions of the engine; hence it is required that the A/F be detected in a wide range from the rich region to the lean region by a single sensor.

On the other hand, relations between the excess air rate $\lambda$ and a residual oxygen consistency and a carbon monoxide consistency in exhaust gas are as shown in FIG. 11 and in the lean region the oxygen ($O_2$) consistency varies approximately linearly to the A/F and in the rich region the carbon monoxide (CO) consistency varies approximately linearly to the A/F.

Basic principles of A/F sensors of the prior art which detect the A/F of each region individually by utilizing the residual oxygen consistency and the carbon monoxide consistency are shown in FIG. 12 (A)–(C). The A/F sensor is constituted by an electrode 1, a zirconia solid electrolyte 2, an electrode 3, a protecting film 4 and an ammeter 5.

The sensor shown in FIG. 12 (A) detects the rich region ($\lambda<1$) by applying an exciting voltage E of approximately 0.5 V between the electrode 1 and the electrode 3 which are a cathode and an anode respectively as known from, for instance, Japanese Patent Laid-Open No. 66292/1978. The protecting film 4 functions as a gas diffusion resistant body and the oxygen gas which is subjected to burning reaction with unburnt gas which is diffused into the electrode 3 part through the protecting film 4 is transferred from the electrode 1 part contacting the atmosphere to the electrode 3 part through the zirconia solid electrolyte 2 in the form of oxygen ions. Therefore, a pumping current Ip measured by the ammeter 5 represents the quantity of the oxygen ions transferred from the electrode 1 to the electrode 3 and corresponds to the quantity of the unburnt gas diffused into the electrode 3 part through the protecting film 4 so that the analog detection of the A/F in the rich region in facilitated by measurement of Ip.

As shown in FIG. 12 (B), when an electromotive force e$\lambda$ between two electrodes is detected with the potential of the electrode 3 contacting the exhaust gas through the protecting film as reference, because the value of e$\lambda$ changes incrementally by approximately i V at the theoretical F/N, the approximate digital detection of $\lambda=1$ is facilitated by measurement of e$\lambda$. This principle is known from, for instance, Japanese Patent Laid-Open No. 37599/1972.

As shown in FIG. 12 (C), when an exciting voltage of approximately 0.5 V is applied between two electrodes with the electrode 3 as a cathode, the oxygen ions are pumped from the electrode 3 part to the electrode 1 part and the pumping current Ip is measured by the ammeter 5. As this pumping current Ip corresponds to the quantity of the oxygen diffused into the electrode 3 part through the protecting film, the lean region ($\lambda>1$) can be detected from the Ip value. This principle is known from, for instance, Japanese Patent Laid-Open No. 69690/1977.

Examples of the characteristics of the sensors of the prior art shown in FIG. (A)–(C) are shown in FIG. 13. The characteristic in the lean region is shown by a one-dot-chain line, the characteristic in the rich region is shown by a dotted line and the characteristic at the theoretical A/F is shown by a solid line. Thus the detection methods which can detect individual regions are known but the constitution with which the A/F is detected smoothly in the wide range by a single method is not proposed yet.

Note that, as the principle of the sensor shown in FIG. 12 (B) is not based upon the speed of diffusion rule, the rate of the gas diffusion resistance of the protecting film 4 of the sensor of FIG. 12 (B) is formed to be smaller than those of the sensors of FIG. (A) and (C). In general, the thickness of the protecting film 4 in the case of FIG. 12 (B) is formed thinner than those in other cases.

It is also known from, for instance, Japanese Patent Laid-Open No. 62349/1980 and Japanese Patent Laid-Open No. 154450/1980 that analog detection of A/F can be obtained from a terminal voltage between two electrodes by applying a certain current between the electrodes and it is also shown that the A/Fs in the rich region and the lean region can be detected by switching the polarities of two electrodes. However, it is not shown when and how the polarities must be switched.

It is also known from Japanese Patent Laid-Open No. 48749/1983 that the theoretical A/F and the A/F in the lean region can be detected by switching the connection between two electrodes and an electronic circuit and changing the measurement mode of the sensor. However, detection in the rich region is not considered in this method.

OBJECT OF THE INVENTION

It is an object of the present invention to provide an A/F sensor for an automobile by which the A/F in a rich region, the A/F at a theoretical A/F in a lean region can be detected with a simple constitution and high accuracy.

SUMMARY OF THE INVENTION

In an A/F sensor of the present invention, an electrical potential of an electrode provided on the exhaust side of a zirconia solid electrolyte composing a detecting part is predetermined at the level higher than the ground level of a driving circuit which drives the detecting part and an exciting voltage between an electrode on the atmosphere side and the electrode on the exhaust side constituting the detecting part is subjected to feed-back control by the driving circuit. With this constitution, the A/F in a rich region, at a theoretical A/F and in a lean region can be detected continuously from the quantity of oxygen flowing through the zirconia solid electrolyte.

PREFERRED EMBODIMENTS OF THE INVENTION

Embodiments of an A/F sensor of the present invention will be hereinunder described with reference to related drawings.

Figure 14:
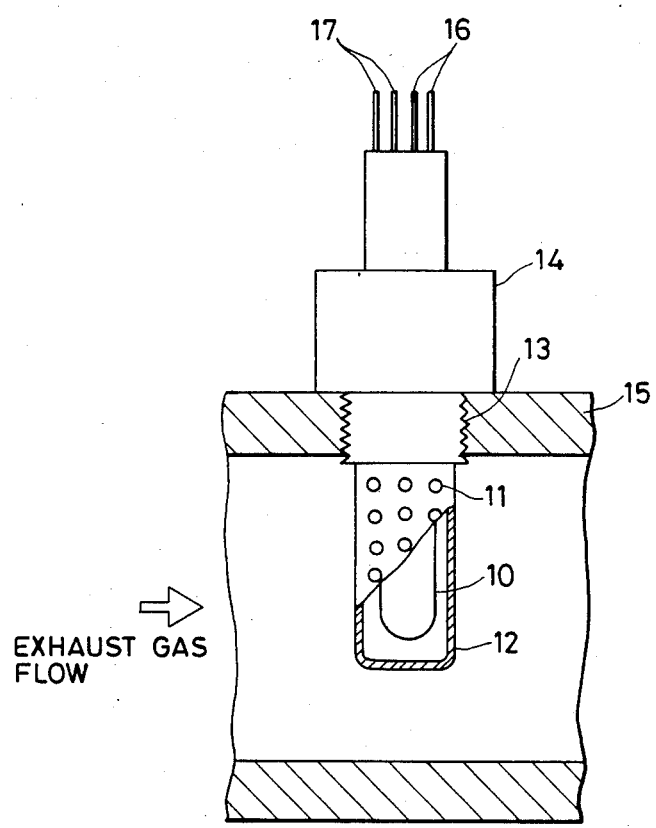
FIG. 14 shows mounting state of an A/F sensor of the present invention.

FIG. 14 shows the mounting state of an A/F sensor of the present invention. A tubular detecting part 10 is provided in a protecting tube 12 which has holes 11 and fixed in a peg 14 and mounted in an exhaust pipe 15 through which exhaust gas is flowing. The reference numeral 16 denotes electrode terminals and the reference numeral 17 denotes heater terminals through which the detecting part 10 is connected to an electronic circuit (not shown). A rod shaped heater (such as a tungsten heater mounted in an alumina rod) is mounted in a zirconia solid electrolyte 10 composing a tubular detecting part.

Before describing the embodiments of the present invention, the basic principle of the present invention will be described hereinunder with reference to FIG. 1 and FIG. 2.

Figure 2:
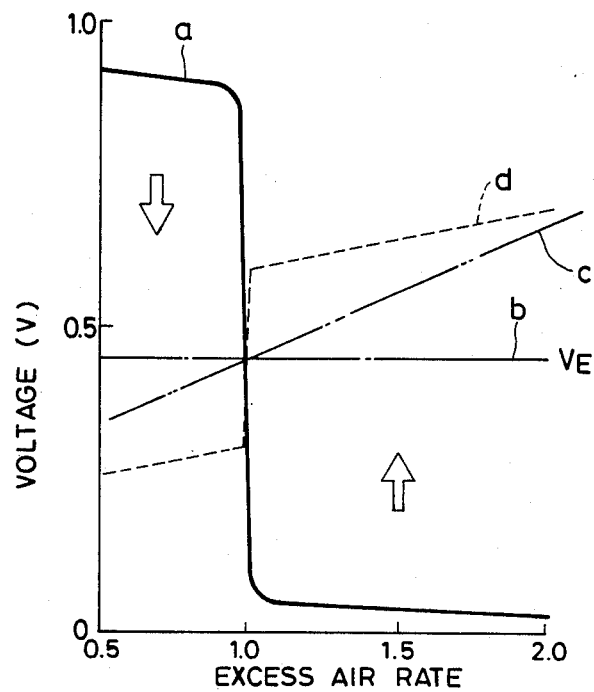
FIG. 2 is an electromotive force characteristic diagram describing the principle of the present invention.

A predetermined voltage $V_E$ (for instance 0.45 V) is applied between an electrode on the atmosphere side and an electrode on the exhaust side regardless of an excess air rate λ such as shown by an exciting voltage characteristic (b) in FIG. 2 against a characteristic of a curve (a) which changes incrementally at the theoretical A/F (λ=1). With this applied voltage, an electromotive force of the curve (a) is decreased in a rich region (λ>1). The voltage $V_E$ can be applied with a predetermined inclination as shown by characteristic (c) or incrementally as shown by characteristic (b).

Figure 1:
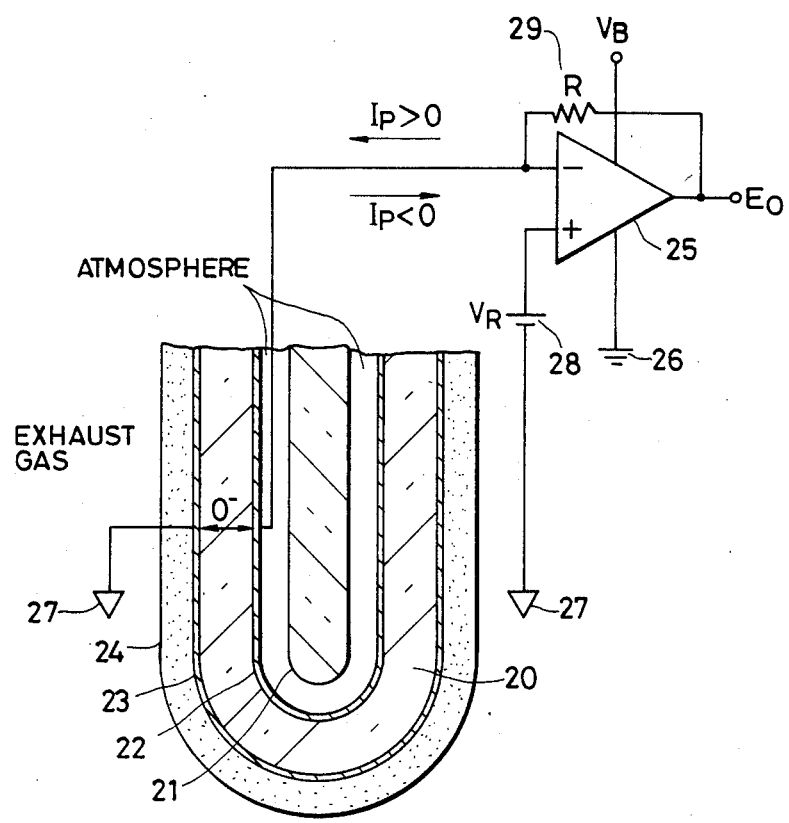
FIG. 1 shows a principle constitution of an A/F sensor of the present invention.

FIG. 1 shows a principle constitution of the present invention. The sensor of FIG. 1 is constituted by a detecting part of oxygen constituency and a driving circuit which drives the detecting part. The reference numeral 20 denotes a tubular zirconia solid electrolyte and the atmospheric air is introduced into the electrolyte 20. The reference numeral 21 denotes a rod-shaped heater which heats the zirconia solid electrolyte 20 to at least 600° C. to improve conductiveness of oxygen ions. A first electrode 22 is formed on the atmosphere side of the zirconia solid electrolyte 20 and a second electrode 23 is formed on the exhaust side of the zirconia solid electrolyte 20. These electrodes are composed of platinum with thickness of several tens of um and made porous. A diffusion-resistant body 24 is formed on the surface of the second electrode 23 to suppress gases such as oxygen or carbon monoxide which flow from the exhaust gas atmosphere into the electrode 23 part by diffusion. The diffusion-resistant body 24 is formed by plasma spray from a spinner or the like and made porous. In order to make the diffusion resistance rate large, the thickness of the diffusion resistant body 24 is several hundreds of um and has a thickness several times that of the film in a theoretical A/F sensor. The detecting part of the A/F sensor is constituted as described above.

The reference numeral 25 denotes a differential amplifier. The second electrode 23 is connected to a floating ground 27 which has a level higher by a certain voltage than a real ground 26. The first electrode 22 is connected to a (−) side input terminal of the amplifier 25. A voltage source 28 for predetermination of an exciting voltage $V_R$ is inserted between a (+) side input terminal of the amplifier 25 and the floating ground 27. A fixed resistor 29 of resistance R is provided for converting an oxygen pumping current Ip which represents the quantity of oxygen ions flowing through the zirconia solid electrolyte 20 into an output voltage Eo. The driving circuit of the A/F sensor is constituted as described above.

The operation of the A/F sensor of the present invention is hereinunder described.

As a potential of the second electrode 23 is lower than a potential of the first electrode 22 by $V_R$ in the lean region, oxygen molecules in the second electrode 23 part are converted into oxygen ions (o⁻) in the electrode part by the exciting voltage $V_R$ and transferred to the first electrode 22 part through the zirconia solid electrolyte 20 by an operation of oxygen pump. Then the oxygen ions are again neutralized in the electrode part and discharged into the atmosphere. At that time, a positive pump current Ip (reverse direction to o⁻flow) is applied in the circuit and the output voltage Eo is changed.

As the pumping current Ip, wherein Ip>0, corresponds to the quantity of oxygen flowing from the exhaust gas atmosphere into the second electrode 23 part through the diffusion resistant body 24 by diffusion, the following equation is effected:

$$Ip = K(\lambda - 1) \quad (1)$$

wherein λ is an excess air rate and K is proportionality constant.

Therefore, if an electrical potential of the potential ground is Vo, as the output voltage Eo of the A/F sensor is, $$Eo = V_R + Vo + IpR \quad (2)$$

then from equations (1) and (2), $$Eo = V_R + Vo + K(\lambda - 1)R \quad (3)$$

At the theoretical A/F (λ=1), the ratio of the residual oxygen and the residual unburnt gas such as carbon monoxide in the exhaust gas flowing into the second electrode 23 part through the diffusion resistant body is the ratio of the chemical equivalents and both of them are completely burnt by catalysis of the second electrode. As the oxygen is eliminated in the second electrode 23 part, even if a voltage is applied between the first electrode 22 and the second electrode 23, no oxygen ion is transferred through the zirconia solid electrolyte 20. Therefore, the pumping current in the electronic circuit becomes zero (Ip=0).

At that time, from the equation (3), the output voltage Eo is, $$Eo = V_R + Vo \quad (4)$$

which is a constant value determined only by circuit constants. As the question (4) is independent of Ip, the output voltage Eo at $\lambda = 1$ is a highly reliable value.

In the rich region, as the electromotive force between two electrodes is reduced to the level of the exciting voltage as described in FIG. 2, the oxygen ions flow from the first electrode 22 part into the second electrode 23 part through the zirconia solid electrolyte 20, or flow in the opposite direction to the case of the lean region. The oxygen ion flow increases oxygen consistency in the second electrode 23 part. The oxygen ions are again neutralized in the second electrode 23 part to be converted into oxygen molecules and are burnt with the unburnt gas such as carbon monoxide which flows from the exhaust gas atmosphere into the second electrode 23 part through the diffusion resistant body 24.

Therefore, the quantity of the oxygen ions transferred from the first electrode 22 part to the second electrode 23 through the zirconia solid electrolyte 20 corresponds to the quantity of the unburnt gas flowing into the second electrode 23 part by diffusion. At that time, the pumping current in the electronic circuit is Ip<0.

Figure 11:
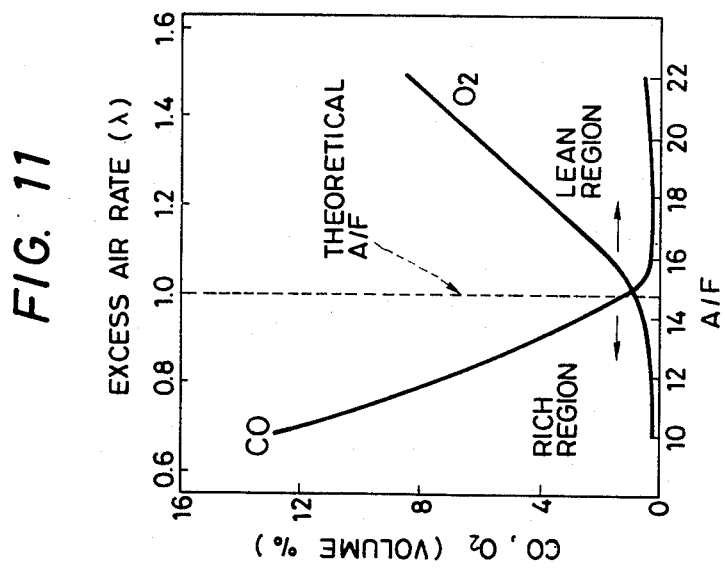
FIG. 11 shows relations between A/F and exhaust gas consistencies.
Figure 12A:
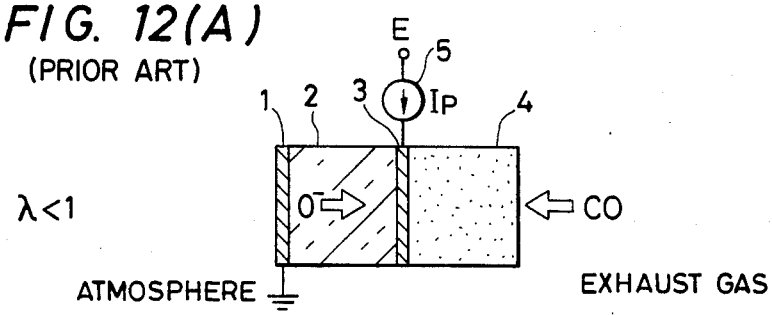
FIGS. 12 a, b and c describe principles of A/F sensors of the prior art.
Figure 12B:
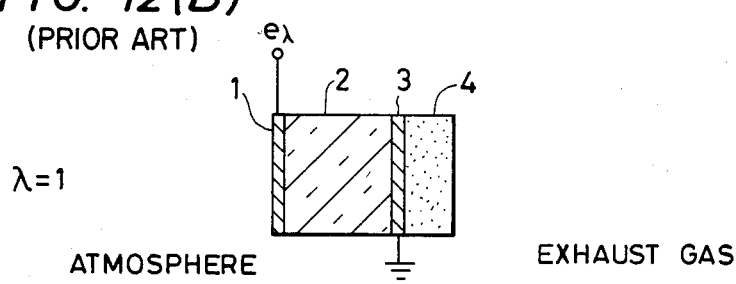
Figure 12C:
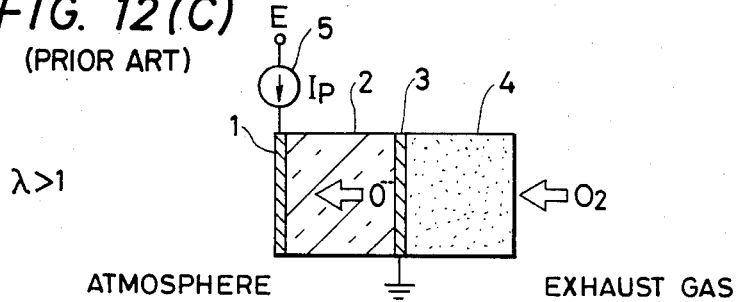

As there is a certain relation between the consistency of the unburnt gas such as carbon monoxide and the excess air rate $\lambda$ as shown in FIG. 11, equations (1)-(3) are effective in the rich region too, except that in the lean region, as $\lambda > 1$, then Ip>0 and in the rich region, as $\lambda < 1$, then Ip<0.

Then one embodiment of a driving circuit of an A/F sensor of the present invention is hereinunder described with reference to FIG. 3. The same parts as in FIG. 1 are denoted by the same reference numerals as in FIG. 1.

The second electrode 23 is connected to the potential ground 27 (point Y) and controlled at a constant potential Vo by an amplifier 30. The potential of the first electrode 22 is controlled to be (Vo+$V_R$) by an amplifier 25. Therefore, the potential difference between the first electrode 22 and the second electrode 23, or the exciting voltage $V_E$ is, $$V_E = (Vo + V_R) - Vo = V_R \quad (5)$$

and is controlled at a constant value regardless of the excess air rate $\lambda$.

In the lean region, the pumping current Ip flows from a point X to the real ground 26 through the resistor 29—the zirconia solid electrolyte 20—the floating ground point Y→the amplifier 30.

In the rich region, the pumping current Ip flows from the floating ground point Y to the real ground 26 through the zirconia solid electrolyte 20→the resistor 29→the point X→the amplifier 25.

At the theoretical A/F ($\lambda = 1$), in the sensor Ip=0 as the principle, the output voltage Eo becomes ($V_R + Vo$) as given by the equation (4).

Thus, with the embodiment of an A/F sensor of the present invention three conditions, i.e. $\lambda < 1$, $\lambda = 1$ and $\lambda > 1$ can be detected continuously without switching the polarities between two electrodes and with a single source circuit.

Figure 3:
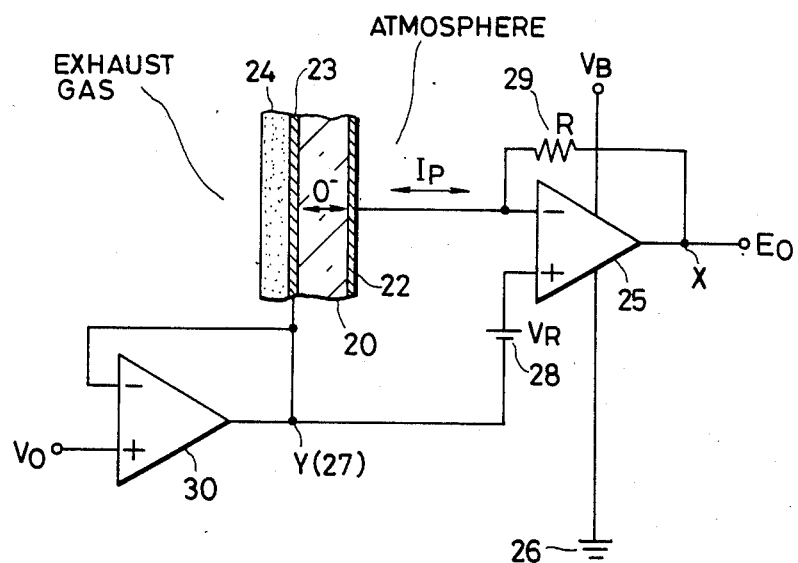
FIG. 3 shows a circuit configuration describing one embodiment of an A/F sensor of the present invention.
Figure 4:
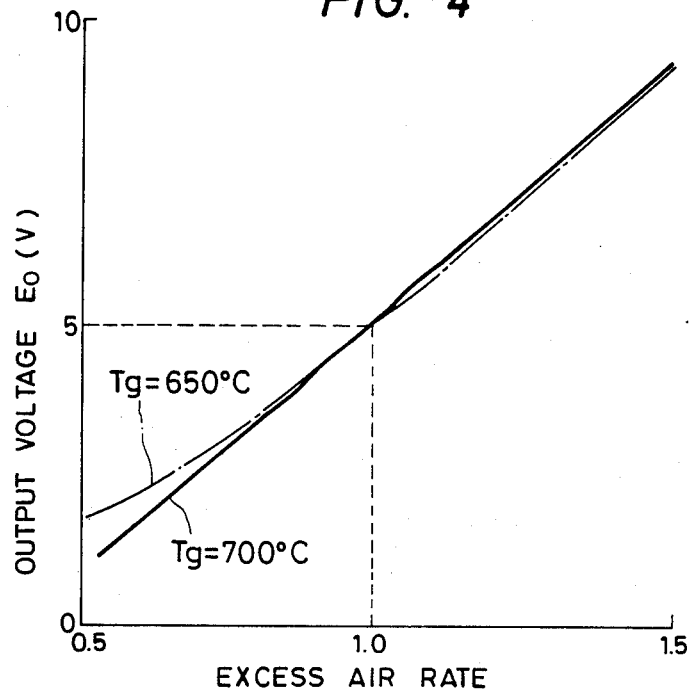
FIG. 4 shows examples of characteristics of an A/F sensor of the present invention.

Examples of the results obtained by the measurement with the constitution of the embodiment of the present invention shown in FIG. 3 are shown in FIG. 4. FIG. 4 shows the measured results when Vo=4.55 V and $V_R$=0.45 V. As shown by a solid line in the diagram, the A/F can be detected in the wide range from the rich region to the lean region continuously. It was also confirmed that the output voltage Eo at the theoretical A/F ($\lambda = 1$) was Vo+$V_R$=5 V which was predicted from the principle.

With this embodiment, the A/F in the whole regions can be detected linearly and with high accuracy and smooth feed-back control A/F is facilitated in accordance with the conditions of an engine and a far more excellent control system in terms of exhaust gas countermeasure and fuel economy, compared to systems of the prior art, can be provided. Especially, significant improvement of fuel efficiency can be expected by that engine control in the lean region is facilitated and that linear feed-back control in the rich region is facilitated.

Figure 5:
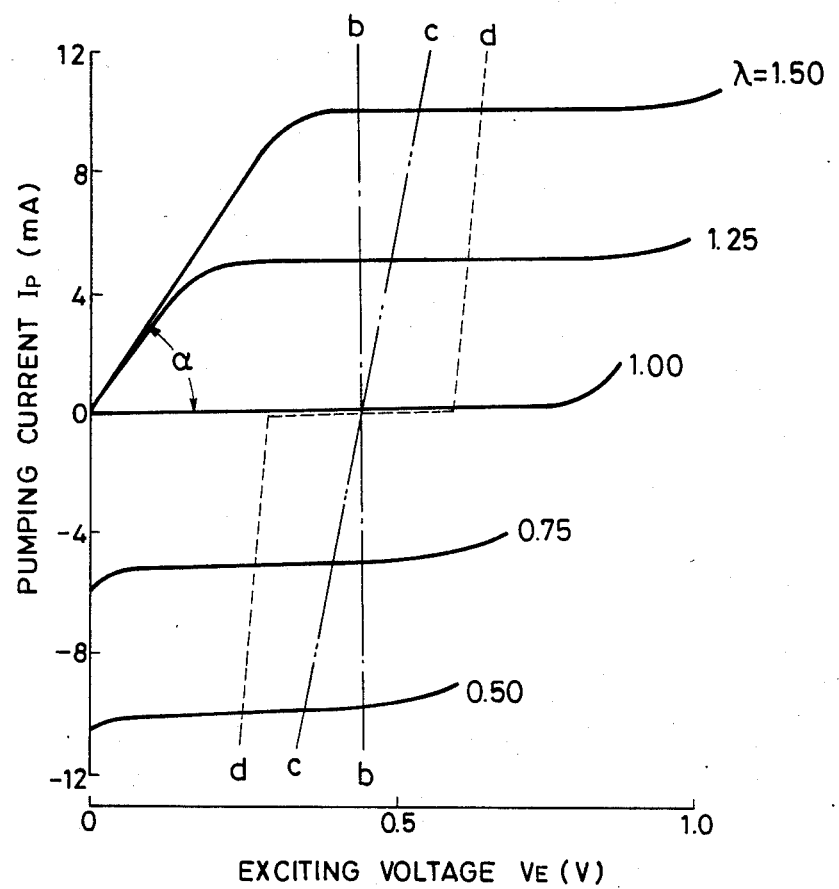
FIG. 5 shows examples of V-I characteristics.

V-I characteristics of the sensor detecting part are shown in FIG. 5.

As shown in the diagram, a pumping current Ip shows a certain saturated value at a certain exciting voltage. By measuring the saturated current value, the excess air rate $\lambda$ can be detected. If the exciting voltage $V_E$ goes higher, the pumping current Ip shows a higher value than the saturated value. This phenomenon is caused by a shift of the conduction mechanism in the zirconia solid electrolyte 20 from ion conduction to electron conduction. The smaller the exces air rate, the lower the exciting voltage $V_E$ at which shift to the electron conduction occurs.

In the region of $\lambda > 1$, the pumping current Ip>0 and corresponds to the quantity of oxygen flowing into the second electrode 23 part by diffusion through the diffusion resistant body 24. In the region of $\lambda < 1$, the pumping current Ip<0 and corresponds to the quantity of unburnt gas such as carbon monoxide flowing into the second electrode 23 part by diffusion through the diffusion resistant body 24. FIG. 5 shows V-I characteristics when the temperature Tg of the zirconia solid electrolyte is 700° C.

If the saturated current Ip corresponding to each excess air rate can be detected, the A/F can be detected linearly in the wide range from the rich region to the lean region. As understood from the V-I characteristics shown in FIG. 5, these saturated current values can be measured by predetermining the characteristic (b), the characteristic (c) or the characteristic (d) as the exciting voltage characteristic to the excess air rate.

If the exciting voltage characteristic is (b), measurement of the saturated current near $\lambda = 0.5$ and $\lambda = 1.5$ is difficult. This problem is solved by converting the exciting characteristic into (c), or preferably (d).

As internal resistance of the zirconia solid electrolyte increases when the temperature decreases, the region of the V-I characteristic $\alpha$ becomes narrow. Therefore, measurement of the saturated current tends to be difficult at the low temperature. This tendency is the most noticeable with the characteristic (b). To solve the problem, the zirconia solid electrolyte must be heated to high temperature by a heater. It is recommended to heat the zirconia solid electrolyte with the heater to a temperature not less than approximately 750° C., 700° C. and 670° C. when the exciting voltage characteristic is (b), (c) and (d) respectively. Taking the power consumption and the durability of the heater into account, the characteristic (c) is preferred to (b) and (d) is preferred to (c).

These exciting voltage characteristics (b), (c) and (d) correspond to the characteristics (b), (c) and (d) shown in FIG. 2 respectively.

Figure 6:
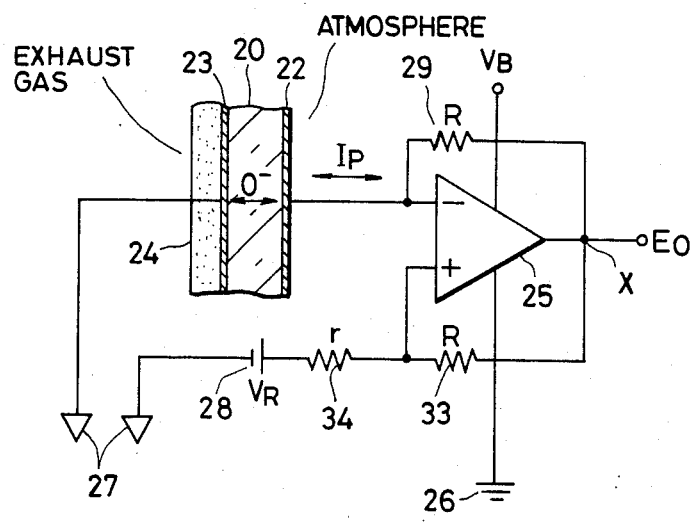
FIG. 6 shows the other embodiment of an A/F sensor of the present invention.

FIG. 6 shows one embodiment of the present invention with which the exciting voltage characteristic (c) shown in FIG. 2 is obtained, wherein a resistor 33 and resistor 34 are inserted between the source 28 and the point X of the configuration given by FIG. 3. As a result, a potential difference rIp is produced in the resistor 34 part in accordance with the output voltage Eo changed by the pumping current Ip and the potential difference between the first electrode 22 and the second electrode 23, or the exciting voltage between two electrodes, is changed by this value. If the resistance (r) of the resistor 34 is predetermined to be close to the internal resistance of the zirconia solid electrolyte 20, the output voltage Eo of the A/F sensor is less influenced by the temperature of the exhaust gas. As the potential difference rIp is changed not only by the resistance (r) but also by the pumping current Ip, it is automatically changed by the excess air rate λ and the potential difference between two electrodes or the exciting voltage $V_E$ shows the characteristic (c) shown in FIG. 2. With this constitution, temperature dependency of the oxygen ion conduction rate in the zirconia solid electrolyte is improved.

Figure 7:
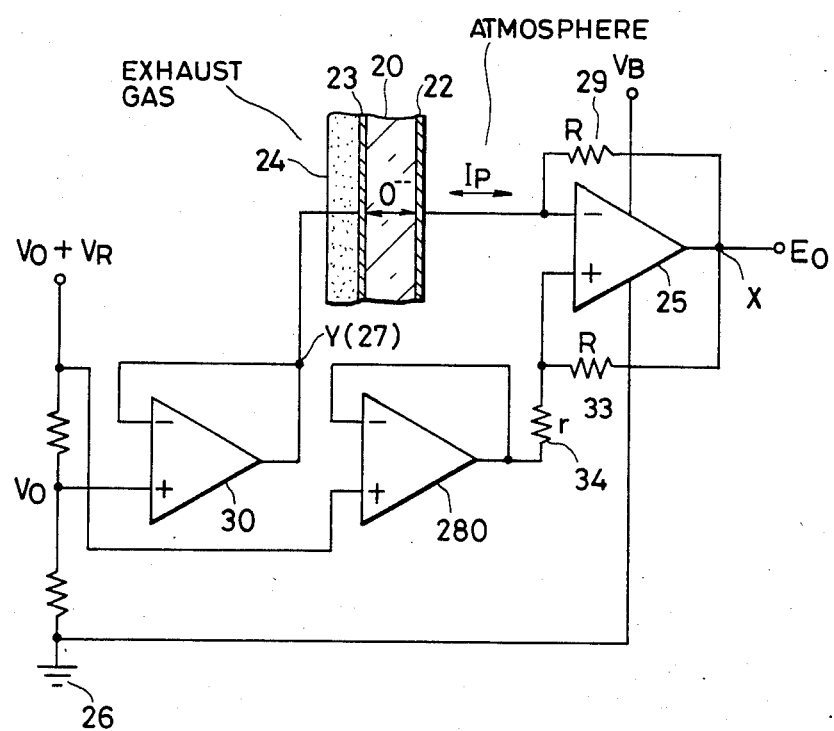
FIG. 7 and FIG. 8 show still other embodiments of an A/F sensor of the present invention.

An embodiment other than shown in FIG. 6 is shown in FIG. 7. An amplifier 280 has the same function as the source 28 in FIG. 3. With this circuit configuration, even if the temperature Tg of the zirconia solid electrolyte 20 is 650° C., the output characteristic is identical to that of the solid line in FIG. 4. Therefore, this configuration is also effective as a countermeasure against the influence of temperature.

Figure 8:
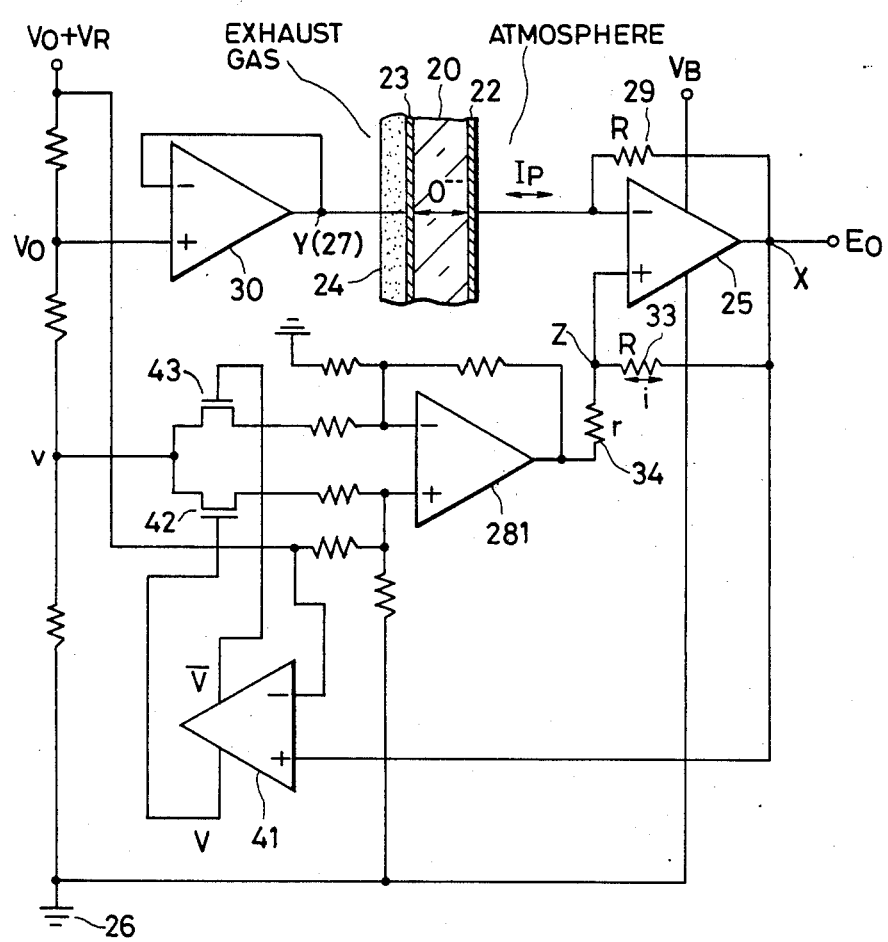

FIG. 8 shows one embodiment of the present invention with which the exciting voltage characteristic (d) shown in FIG. 2 is obtained, wherein basically an amplifier 281 for addition and subtraction, a dual-output comparator 41 and switches 42 and 43 are added to the configuration of FIG. 7. The switches 42 and 43 are driven by output signals V and V of the dual-output comparator 41 which are reversed at the instance of the pumping current Ip=0 and a voltage (v) is supplied to a (+) side input terminal and a (−) side input terminal of the amplifier 281 for addition and subtraction alternately. Taking V* as a potential at the (+) side input terminal part Z of the amplifier 25 and (i) as the current in the resistor 33 part.

$$V^* = Vo + V_R + v + ri \text{ at } \lambda > 1$$

$$V^* = Vo + V_R - v + ri \text{ at } \lambda < 1 \tag{6}$$

With such circuit configuration, the exciting voltage characteristic between two electrodes as given by the characteristic (d) in FIG. 2 can be obtained. Therefore, it is easily understood from the V-I characteristic (d) is suitable for detecting the saturated pumping current Ip corresponding to each excess air rate λ.

Figure 9:
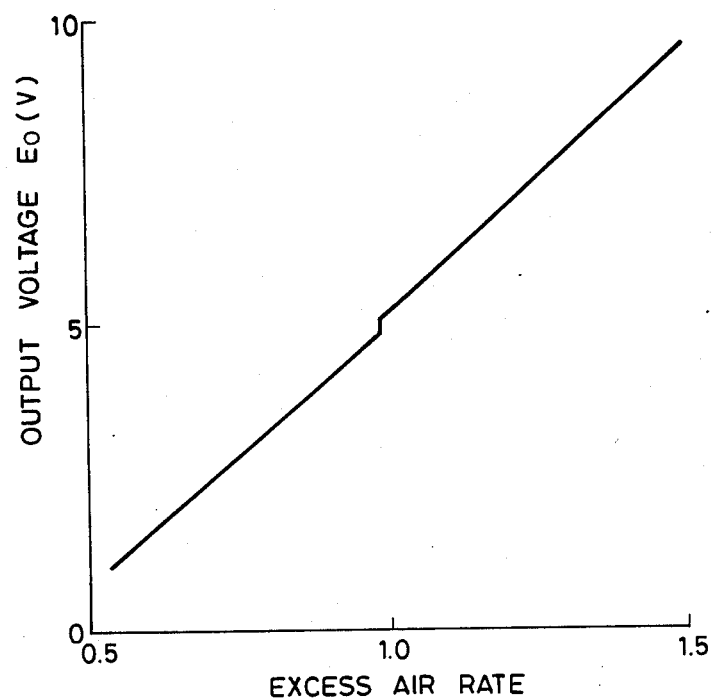
FIG. 9 shows an example of the other characteristic of an A/F sensor of the present invention.

One example of the obtained result measured by the circuit configuration of FIG. 8 is shown in FIG. 9. This diagram shows the measured result when v=0.15 V. In this case, as shown in the diagram, the output voltage Eo changes in step by 2 V at the theoretical A/F, λ=1.

The stepping change of 2 V is not a substantial problem in this embodiment and, if 2 V is added to the characteristic shown in FIG. 2 in the region of λ1, the characteristic of the exciting voltage Eo becomes linear in all regions.

With the constitution of this embodiment, an effect can be obtained which limits the decline of accuracy caused by the deterioration of the electrode (increase of interfacial resistance.)

It is to be noted that, although the form of the zirconia solid electrolyte of the detecting part of the A/F sensor is described as tubular in the above description, it is not to be construed as limiting the scope of the invention. In other words, any structure such as a flat plate type shown in FIG. 10 with which the ambient atmosphere can be introduced into the first electrode part may be accepted.

Figure 10:
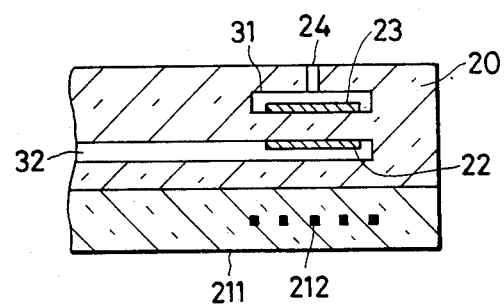
FIG. 10 shows a circuit configuration describing the other embodiment of an A/F sensor of the present invention.
Figure 13:
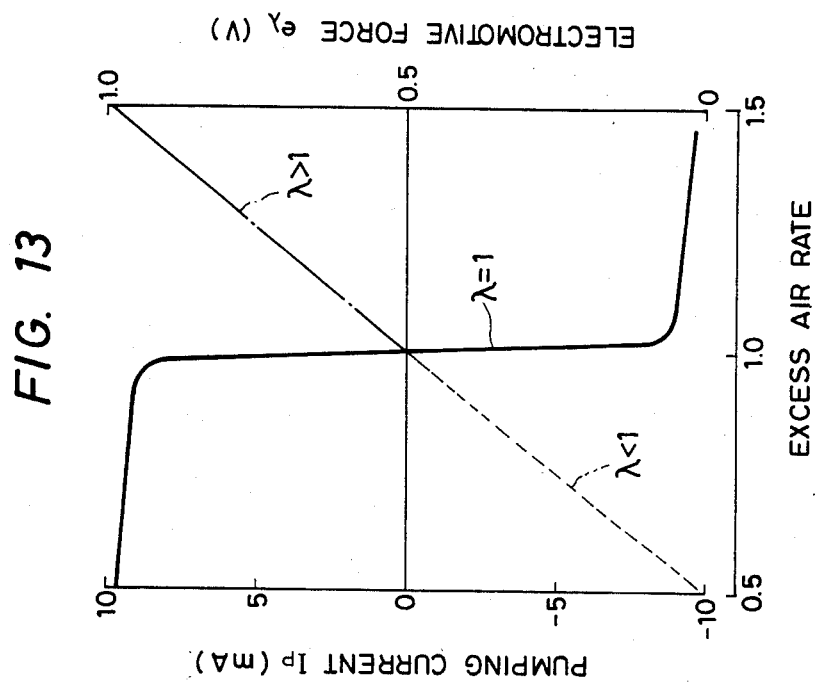
FIG. 13 describes characteristics of A/F sensors of the prior art.

FIG. 10 shows a detecting part, wherein a zirconia solid electrolyte is a flat plate and a diffusion resistant body consists of, for instance, one hole.

In FIG. 10, the same reference numerals as in FIG. 1 denote the parts which have the same function as in FIG. 1. The atmospheric air is introduced into the first electrode 22 part through a passage 32. Residual oxygen and unburnt gas in the exhaust gas flow into the second electrode 23 part in a diffusion chamber 31 by diffusion through a tubular diffusion-resistant body 24. The zirconia solid electrolyte 20 is heated and controlled to a high temperature (for instance 600° C.) at which the oxygen ion conduction rate is high.

Effect of the Invention

With the present invention, an A/F sensor which can detect A/F in a wide range of three conditions, a rich region, theoretical A/F and a lean region, with a simple constitution and high accuracy can be provided.

We claim:

1. An air-to-fuel ratio sensor for an automobile, comprising:
    a detecting device having a zirconia solid electrolyte, a first electrode formed on one side of said solid electrolyte and being exposed to the atmosphere, a second electrode formed on an opposite side of said solid electrolyte and a diffusion-resistant body formed on said second electrode and exposed to a gas-to-be measured having varying concentrations of $O_2$ and CO; and
    a driving circuit for driving said detecting device, including first means for applying to said second electrode a first potential above absolute ground, and second means for applying to said first electrode an exciting voltage to control the potential between said first and second electrodes for the varying concentrations of said gas to-be measured, said second means including means for producing an output voltage responsive to a current flowing between said first and second electrodes for indicating the content of $O_2$ or CO in the gas being measured.

2. An air-to-fuel ratio sensor according to claim 1, wherein said second means comprises means for maintaining the potential between said first and second electrodes at a constant predetermined value for the varying concentrations of said gas to-be-measured.

3. An air-to-fuel ratio sensor according to claim 1, wherein said second means comprises means for varying the potential between said first and second electrodes according to a linear characteristic with variation in the concentrations of $O_2$ and CO in said gas to-be-measured.

4. An air-to-fuel ratio sensor according to claim 1, wherein said second means comprises means for controlling the potential between said first and second electrodes to fall within a first range of values when the gas to-be-measured includes $O_2$ and to fall within a second range of values when the gas to-be-measured includes CO.

5. An air-to-fuel ratio sensor according to claim 1, wherein said first means comprises a constant voltage source for providing said first potential above absolute ground.

6. An air-to-fuel ratio sensor according to claim 5, wherein said constant voltage source comprises a differential amplifier having a non-inverting input terminal connected to a source of said first potential above absolute ground and an output terminal connected to said second electrode of said detecting device and an inverting input terminal of said differential amplifier.

7. An air-to-fuel ratio sensor according to claim 1, wherein said second means comprises a differential amplifier having an inverting input terminal connected to said first electrode of said detecting device, a direct current voltage source connected between said second electrode of said detecting device and a non-inverting input terminal of said differential amplifier, and a resistance feedback path connected between the output terminal and the inverting input terminal of said differential amplifier, said output voltage being provided from the output terminal of said differential amplifier.

8. An air-to-fuel ratio sensor according to claim 7, further including a resistor connected in series with said direct current voltage source between said second electrode of said detecting device and said non-inverting input of said differential amplifier, and a second resistive feedback path between the output terminal and the non-inverting input terminal of said differential amplifier.

9. An air-to-fuel ratio sensor according to claim 8, wherein said direct current voltage source is a constant voltage source.

10. An air-to-fuel ratio sensor according to claim 7, wherein said direct current voltage source comprises a further differential amplifier having an output terminal connected to the non-inverting input terminal of said first-mentioned differential amplifier, a source of said exciting voltage connected to a non-inverting input terminal of said further differential amplifier comparison means for detecting whether said current flowing between said first and second electrodes is flowing from said first electrode to said second electrode or vice versa, and means responsive to said comparison means for applying an offset voltage to the non-inverting input of said further differential amplifier when said current is flowing from said first electrode to said second electrode and for applying said offset voltage to an inverting input of said further differential amplifier when said current is flowing from said second electrode to said first electrode.

11. An air-to-fuel ratio sensor according to claim 10, further including a resistor connected in series with said direct current voltage source between said second electrode of said detecting device and said non-inverting input of said differential amplifier, and a second resistive feedback path between the output terminal and the non-inverting input terminal of said differential amplifier.

12. An air-to-fuel ratio sensor according to claim 1, wherein said second means includes means for varying the exciting voltage applied to said first electrode in accordance with the quantity of oxygen ions flowing through said solid electrolyte.

13. An air-to-fuel ratio sensor according to claim 1, wherein said second means includes means for varying the exciting voltage applied to said first electrode between first and second ranges of values in accordance with the direction of the flow of oxygen ions through said solid electrolyte.

* * * * *